United States Patent
Adi et al.

(10) Patent No.: US 9,904,817 B2
(45) Date of Patent: *Feb. 27, 2018

(54) PHYSICAL-INTERACTIVE IDS (P2D)

(71) Applicant: International Business Machines Corporation, Armonk, NY (US)

(72) Inventors: Asaf Adi, Qiryat Ata (IL); David Breitgand, Modiin (IL); Lior Limonad, Nesher (IL); Nir E Mashkif, Ein Carmel (IL); Ari Volcoff, Yokneam Ilit (IL); Alexander Zadorojniy, Haifa (IL); Sergey Zeltyn, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/607,540

(22) Filed: May 29, 2017

(65) Prior Publication Data

US 2017/0351882 A1 Dec. 7, 2017

Related U.S. Application Data

(63) Continuation of application No. 15/169,752, filed on Jun. 1, 2016.

(51) Int. Cl.
*G06K 7/00* (2006.01)
*G06K 7/04* (2006.01)

(52) U.S. Cl.
CPC .................................. *G06K 7/04* (2013.01)

(58) Field of Classification Search
CPC ....... G06K 19/04; B43M 3/045; G06Q 30/02; G06Q 20/341; G07F 7/1008

USPC ......................................... 235/453, 375, 380
See application file for complete search history.

(56) References Cited

U.S. PATENT DOCUMENTS

| | | |
|---|---|---|
| 9,063,537 B2 | 6/2015 | Pastor et al. |
| 9,101,534 B2 | 8/2015 | Bochenko |
| 2015/0100445 A1 | 4/2015 | Johnson et al. |

FOREIGN PATENT DOCUMENTS

| | | | |
|---|---|---|---|
| EP | 2778854 | | 9/2014 |
| WO | WO 44/10650 | * | 5/1994 |
| WO | 2015080773 | | 6/2015 |

OTHER PUBLICATIONS

From LabAutopedia., "Automatic identification and data capture", Jan. 28, 2016, Can be found at: http://www.labautopedia.org/mw/Automatic_identification_and_data_capture.

(Continued)

*Primary Examiner* — Karl D Frech

(57) ABSTRACT

Embodiments of the present invention may provide the capability to identify a specific object being interacted with that may be cheaply and easily included in mass-produced objects. In an embodiment, a computer-implemented method for object identification may comprise receiving a signal produced by a physical interaction with an object to be identified, the signal produced by an identification structure coupled to the object during physical interaction with the object, processing the signal to form digital data identifying the object, and accessing a database using the digital data to retrieve additional information identifying or describing properties of the object identified.

12 Claims, 6 Drawing Sheets

(56) References Cited

OTHER PUBLICATIONS

Chris Harrison et al., "Acoustic Barcodes: Passive, Durable and inexpensive Notched Identification Tags", In Proceedings of the 25th Annual ACM Symposium on User interface Software and Technology (Cambridge, Massachusetts, Oct. 7-10, 2012) UIST '12. ACM, New York, NY. 563-568.
Valkyrie Savage et al., "Lamello: Passive Acoustic Sensing for Tangible Input Components", Published Web Location: http://dx.doi.org/10.1145/2702123.2702207, Publication Date: Aug. 18, 2015.

\* cited by examiner

PHYSICAL-INTERACTIVE IDS (P2D)

CROSS-REFERENCE TO RELATED APPLICATIONS

This application is a continuation of U.S. patent application Ser. No. 15/169,752, filed Jun. 1, 2016.

BACKGROUND

The present invention relates to techniques for detecting a physical interaction signal produced by at least one physical interactive ID structure and determining the identity of the object according to the detected physical interaction signal.

Typically, mass-produced objects share the same form and cannot be distinguished from one another. However, for many uses, it is useful or necessary to be able to distinguish among mass-produced objects. For example, a plastic bottle is a commonly used container for various beverages. However, the same bottle may be used as a container for non-edible or toxic substances, such as detergent. In such situations, it may be necessary to be able distinguish between two similar bottles may be required to ensure each one is properly used based on its actual contents. Another example is in the area of medication administration. In this situation, it is necessary to know whether the user has taken the right pill at the right time. Similarly, another example may be recognizing the opening of a particular door to enable access control. This also requires the ability to determine which specific door entry is attempted.

Conventional approaches may include object tagging techniques such as barcode, RFID, OCR, magnetic strips, and the like. These techniques either require some digital form of encoding or tag to be attached to the object of interest, or require an advanced form of sensing (e.g., optical, radio). The ability to embed these encoding techniques into mass production is limited. Further, the cost of the encoding or tag for each object, as well the cost of sensing equipment, may be significant.

Accordingly, a need arises for techniques by which a specific object being interacted with may be identified that may be cheaply and easily included in mass-produced objects.

SUMMARY

Embodiments of the present invention may provide the capability to identify a specific object being interacted with that may be cheaply and easily included in mass-produced objects. For example, embodiments may involve augmenting physical objects with unique physical structures that emit or create a unique motional or acoustic signal when interacted with. Upon ordinary interaction by the user with the objects, these signals are formed as a result of the interaction, and may then be sensed via conventional motion or sound sensing, such as an accelerometer, to determine the identity of the object interacted with. The augmentation may be realized in a way that does not affect the original use of the object.

In an embodiment of the present invention, a computer-implemented method for object identification may comprise receiving a signal produced by a physical interaction with an object to be identified, the signal produced by an identification structure coupled to the object during physical interaction with the object, processing the signal to form digital data representing the signal, and accessing a database using the digital data to retrieve information identifying the object.

The identification structure may comprise a plurality of bumps or teeth. The signal may comprise a vibration produced by pin or tooth rubbing against the bumps or teeth. The signal may comprise a sound produced by pin or tooth rubbing against the bumps or teeth. The plurality of bumps or teeth may be arranged so as to encode identification information for the object. The signal may only be produced during normal use of the object. The signal may be captured by a device attached to a user. The identification structure may further comprise a portion corresponding to information identifying a manufacturer of the object.

In an embodiment of the present invention, a computer program product for object identification may comprise a non-transitory computer readable storage having program instructions embodied therewith, the program instructions executable by a computer, to cause the computer to perform a method comprising receiving a signal produced by a physical interaction with an object to be identified, the signal produced by an identification structure coupled to the object during physical interaction with the object, processing the signal to form digital data representing the signal, and accessing a database using the digital data to retrieve information identifying the object.

In an embodiment of the present invention, a system for object identification may comprise a processor, memory accessible by the processor, and computer program instructions stored in the memory and executable by the processor to perform receiving a signal produced by a physical interaction with an object to be identified, the signal produced by an identification structure coupled to the object during physical interaction with the object, processing the signal to form digital data representing the signal, and accessing a database using the digital data to retrieve information identifying the object.

In an embodiment of the present invention, an object may comprise at least one identification structure adapted to produce a signal upon physical interaction with the object.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Embodiments of the present invention may provide the capability to identify a specific object being interacted with that may be cheaply and easily included in mass-produced objects. For example, embodiments may involve augmenting physical objects with unique physical structures that emit or create a unique motional or acoustic signal when interacted with. Upon ordinary interaction with the objects, these signals may then be sensed via conventional motion or sound sensing, such as an accelerometer, to determine the identity of the object interacted with. The augmentation may be realized in a way that does not affect the original use of the object.

Two basic types of identification techniques may be considered. A Physical ID (PID) may be a structure that is built into an embodiment of an object, which may be sensed in order to identify the object. An Interactive ID (IID) may be a unique encoding that may be sensed only via ordinary object interactions by a user in order to identify the object. These two concepts may be combined to yield a Physical-Interactive ID (P2D). A Physical-Interactive ID is a structure that is built into an embodiment of an object that may be sensed only via ordinary object interactions by a user in order to identify the object.

In an embodiment, physical objects may be physically augmented with Physical-Interactive ID ("PIID" or "P2D") structures. Such a structure may provide the capability to uniquely identify the augmented object, without negatively affecting the original use and appearance of the object being augmented. The identification may be performed by sensing a product of an interaction with the augmented object, such as vibration, noise, etc., which may be sensed using apparatus such as an accelerometer, microphone, gyroscope, etc.

Figure 1:
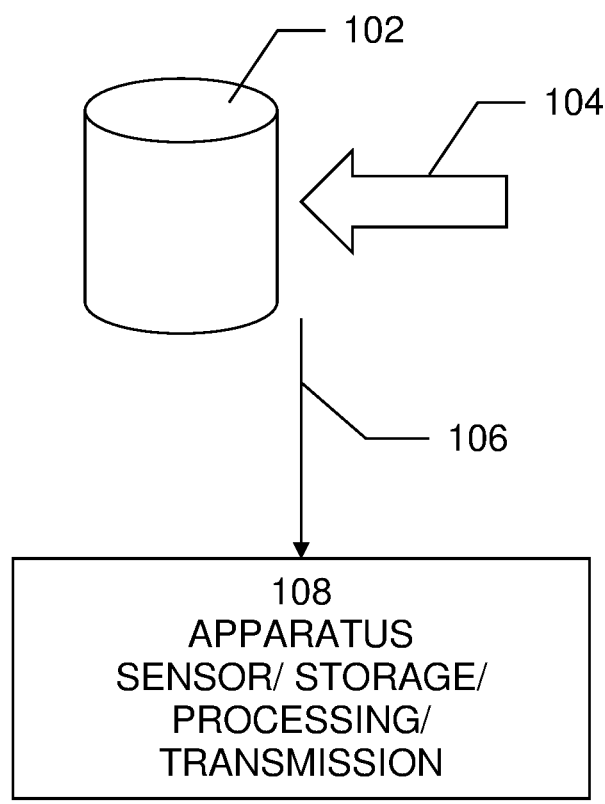
FIG. 1 is an exemplary block diagram of a system for identifying objects that have been physically augmented with Physical-Interactive ID structures.

An exemplary diagram of a system for identifying objects that have been physically augmented with Physical-Interactive ID structures is shown in FIG. 1. In the example shown in FIG. 1, a physically augmented object 102 may be interacted with 104, in a way in which the object is normally interacted with by a user. The product of the interaction, such as vibration, noise, etc. may be received by apparatus 108, which may include one or more sensors, such as an accelerometer, microphone, gyroscope, etc., storage for sensor data, processing circuitry for the sensor data, data transmission circuitry, display circuitry, etc.

Figure 2:
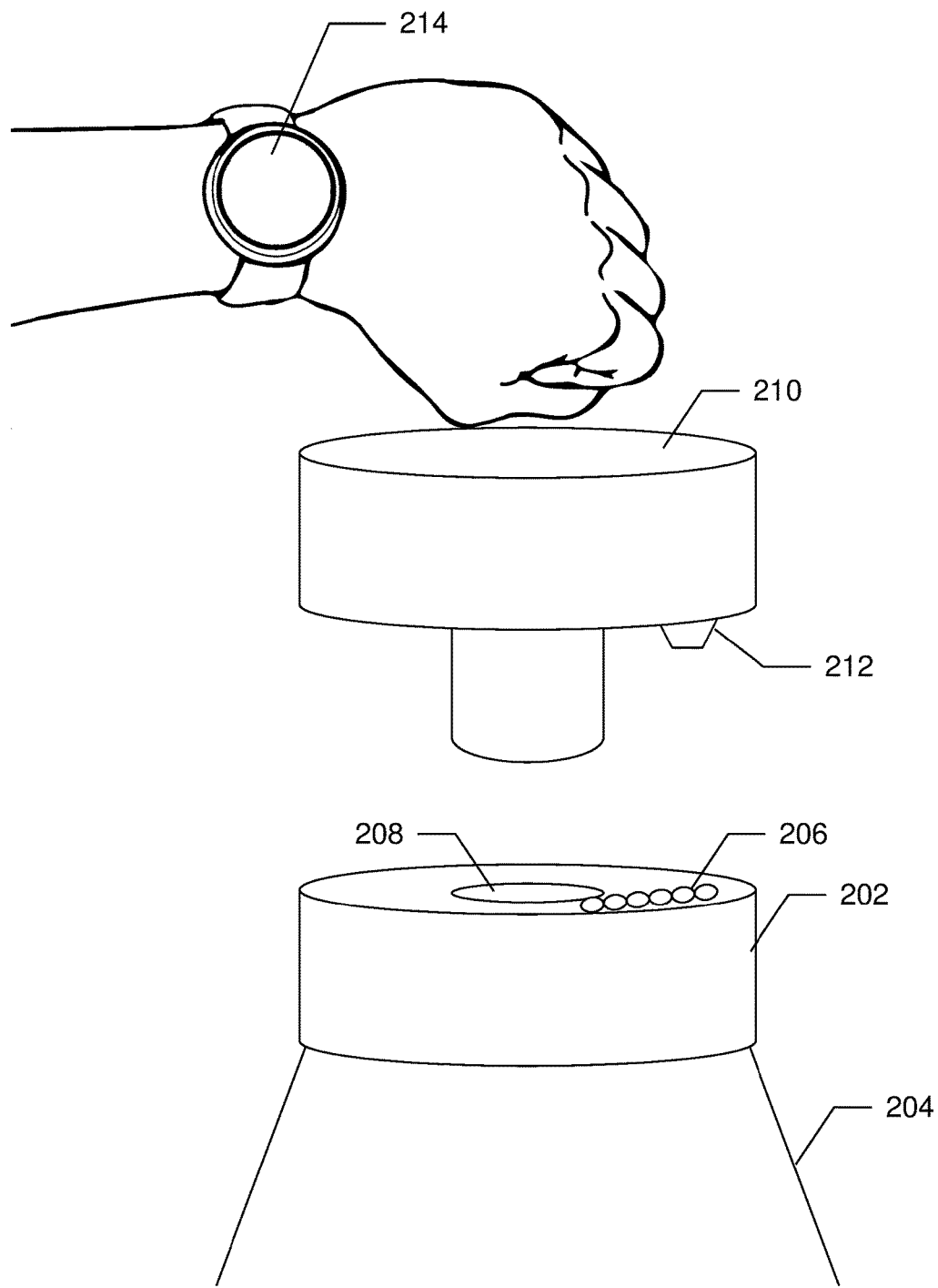
FIG. 2 illustrates an example of an augmented object which may implement an embodiment of the present invention.

An exemplary diagram of an augmented object which may implement an embodiment of the present invention is shown in FIG. 2. In this example, a top portion 202 of a bottle 204 may be augmented with a sequence of structural bumps 206, which are present in or near the neck threads 208 of the bottle 204. The bottle cap 210 may also be augmented with a pin 212 which causes vibration to occur while is being opened or closed. This is due to the interaction of the pin 212 over the series of bumps 206 upon the rotation of the cap 210. The vibration signal may then be picked-up by, for example, a wrist-worn motion and/or sound sensor apparatus 214. Apparatus 214 may correspond to all or a portion of apparatus 108, shown in FIG. 1. This apparatus may provide the basis for using processing or machine learning algorithms similar to those employed for activity and gesture recognition, in order to determine the identity of the object interacted with. It is to be noted that similar or equivalent structures may be deployed into other objects, such as a door handle mechanism, etc. The present invention is not limited to a particular embodiment or structure, but rather contemplates implementation in any embodiment or structure.

Figure 3:
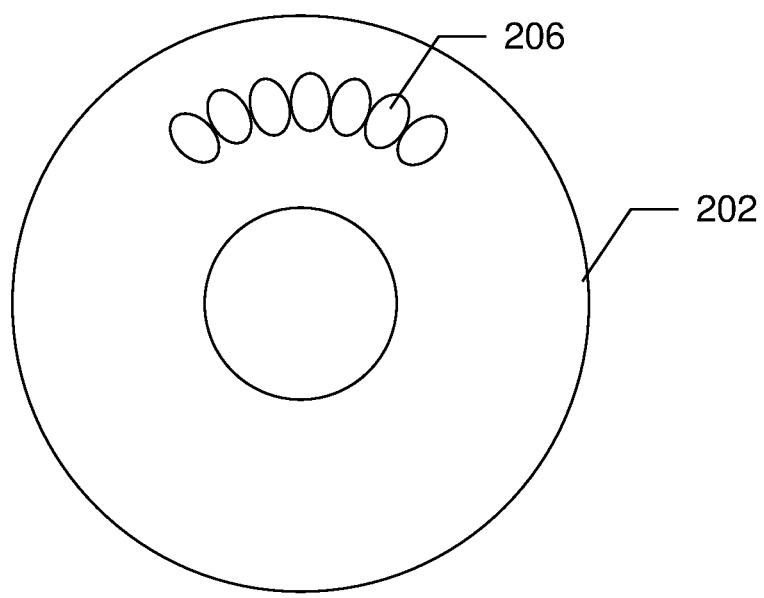
FIG. 3 illustrates an example of a top view of an augmented object.

A top view of an exemplary augmented object shown in FIG. 2 is shown in FIG. 3. In this example, a top portion 202 of the bottle 204 may be augmented with a sequence of structural bumps 206.

Figure 4:
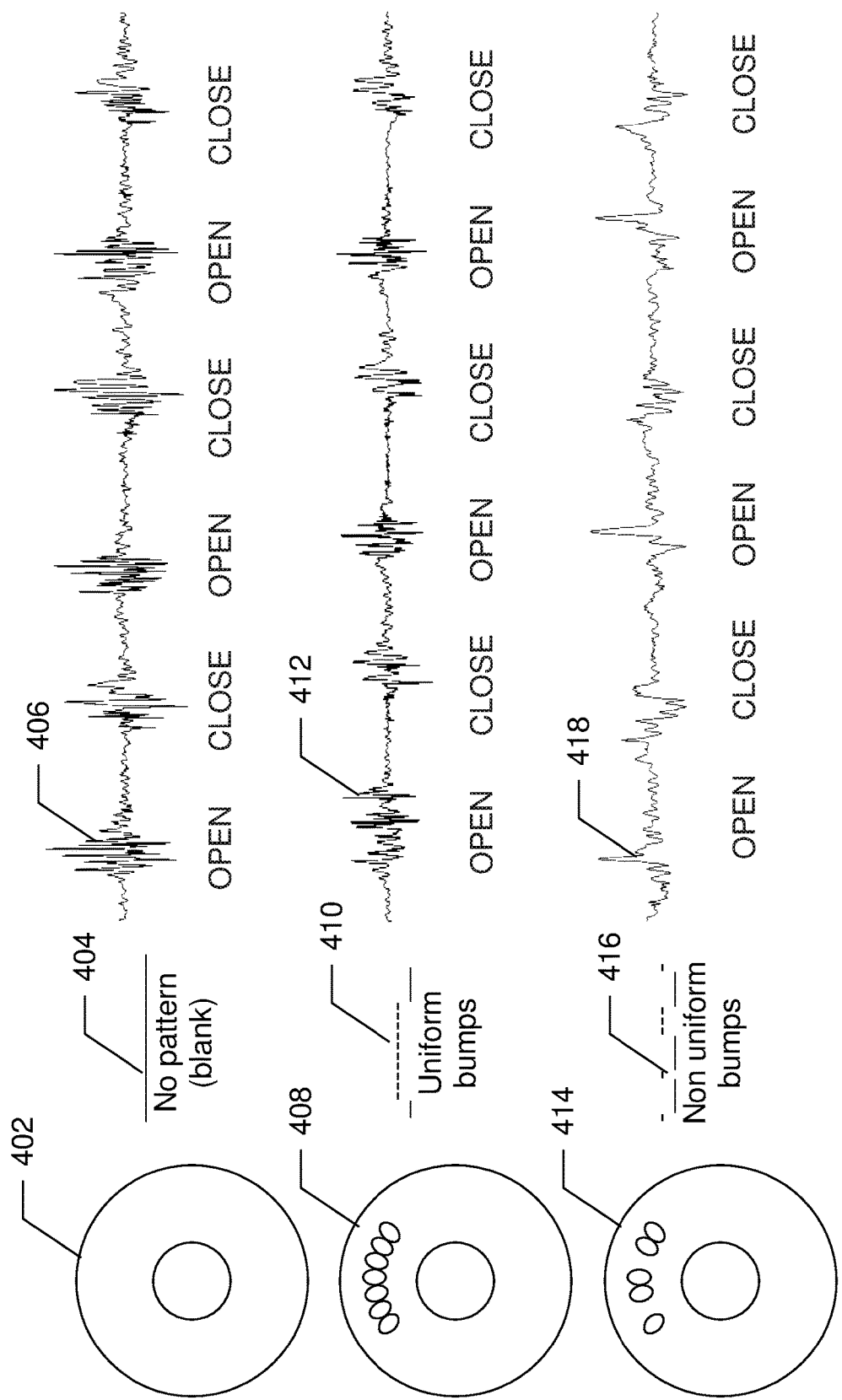
FIG. 4 illustrates examples of vibration signals that may be sensed based on various bump sequence patterns.

Examples of vibration signals that may be sensed based on various bump sequence patterns is shown in FIG. 4. For example, a bump sequence 402 with a blank bump pattern 404 may produce vibration signals 406, as shown for several open/close cycles. A bump sequence 408 with a uniform bump pattern 410 may produce vibration signals 412, as shown for several open/close cycles. A bump sequence 414 with a non-uniform bump pattern 416 may produce vibration signals 418, as shown for several open/close cycles. With suitable processing, these sensed vibration signals may be distinguished and used to identify the augmented object.

Figure 5:
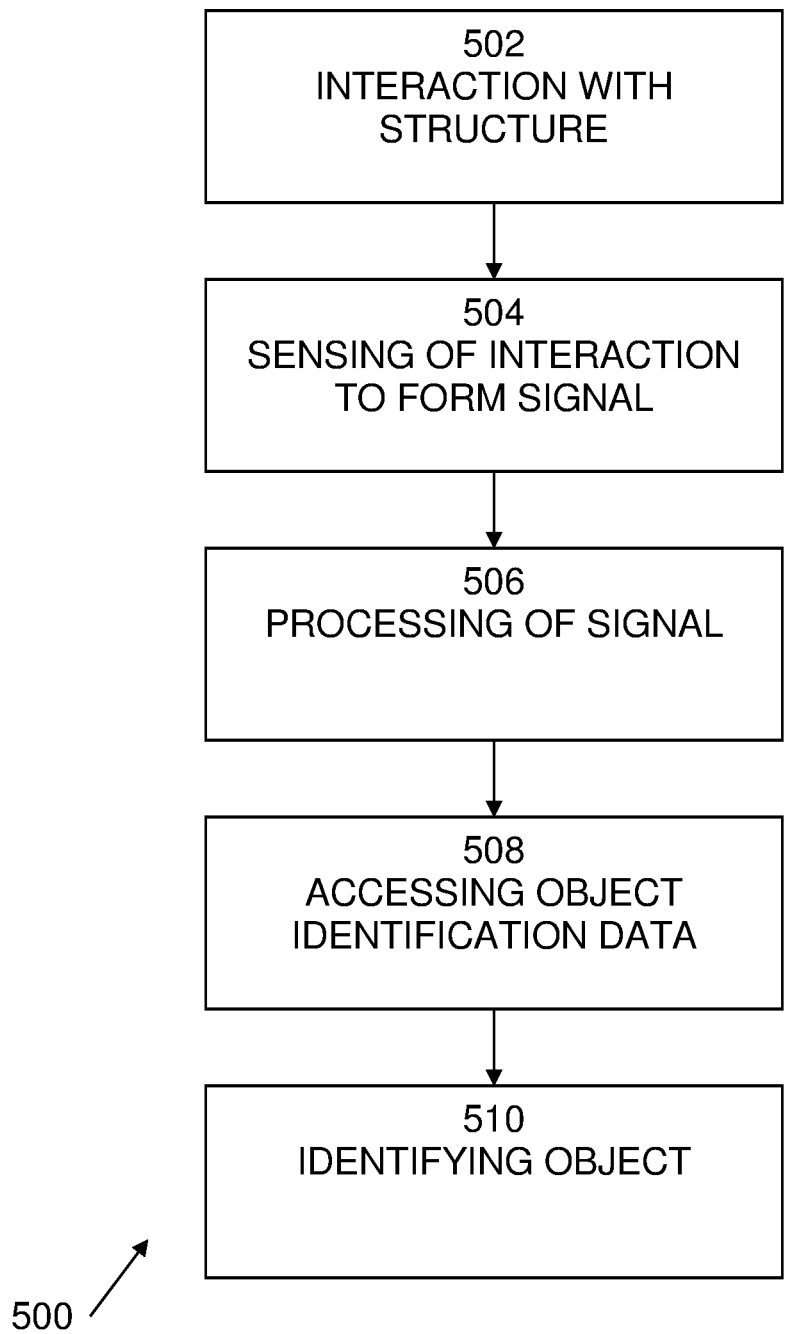
FIG. 5 is an exemplary flow diagram of a process of identifying an object.

A process 500 of identifying an object is shown in FIG. 5. Process 500 begins at 502, in which a physical interaction with the object to be identified may be performed, for example, by a user. At 504, sensing of the interaction may be performed using a sensor to form a signal representing the interaction. For example, the ID structures may be a structural form that yields a unique vibration to the wrist of the user upon the intended interaction with the object, such as is shown in FIGS. 2 and 3 above. This vibration may be sensed by, for example, a wrist-worn motion and/or sound sensor. At 506, the signal produced by the sensor, such as is shown in FIG. 4, may be captured and processed. For example, the signal may be processed to form digital data. At 508, object identification data may be accessed in order to identify the object being interacted with. For example, the processed digital data may be used to access a database that provides the capability to lookup object identity information based on the processed digital data, and at 510, to output information identifying the object. Alternatively, or in addition, the object interacted with may also be augmented with an identification structure, or portion of the existing identification structure, that yields a vibration/sound that may be used for branding purposes. For example, the identification structure may produce a vibration/sound that may be used to identify a manufacturer of the object.

Figure 6:
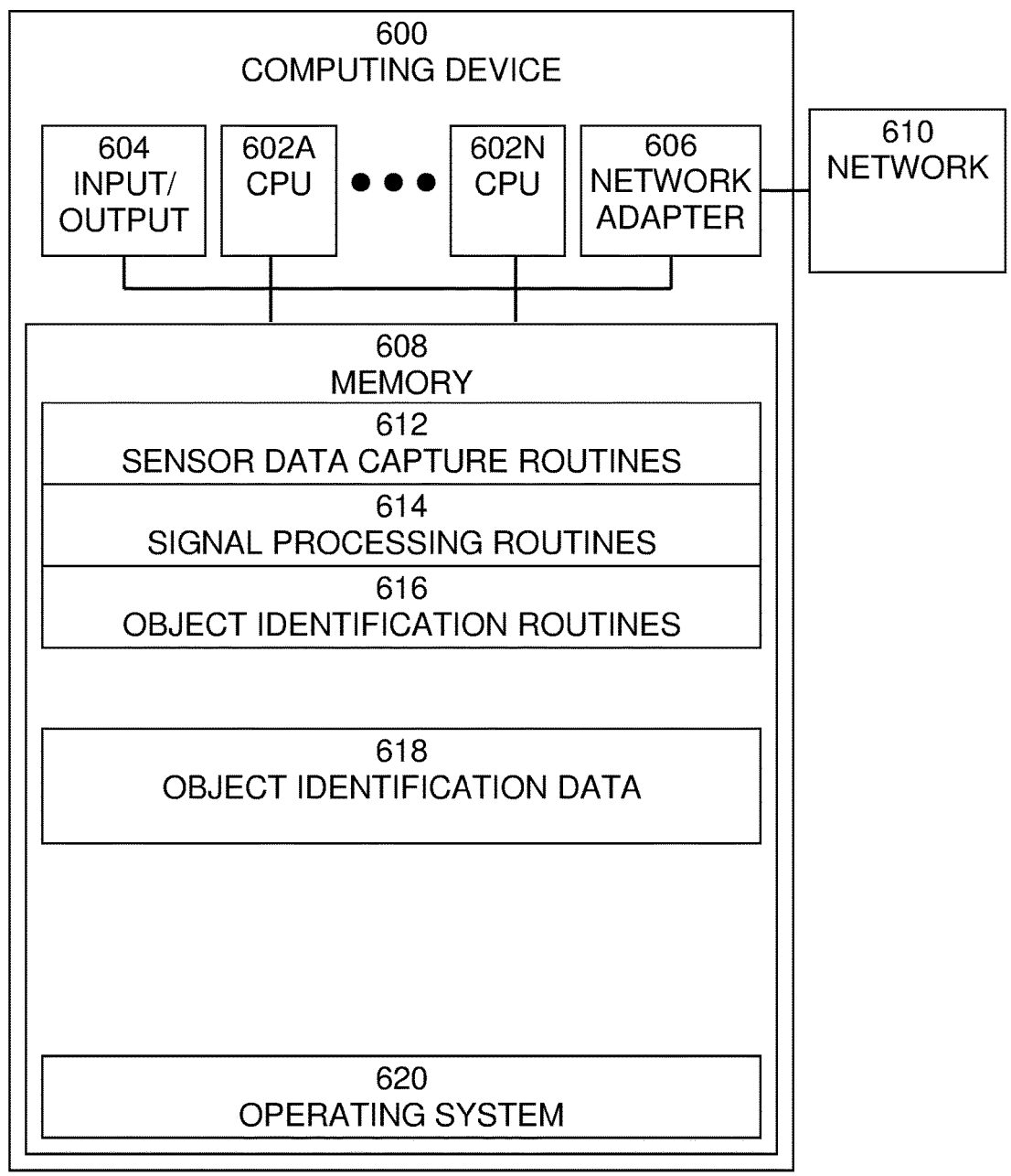
FIG. 6 is an exemplary block diagram of a computer system in which processes involved in the embodiments described herein may be implemented.

An exemplary block diagram of a computing device 600, in which processes involved in the embodiments described herein may be implemented, is shown in FIG. 6. Computing device 600 is typically a programmed general-purpose computer system, such as an embedded processor, system on a chip, personal computer, workstation, server system, and minicomputer or mainframe computer. For example, computing device 600 may be implemented in a wrist-worn, or other personal or mobile device, and may include sensor circuitry as well as display circuitry to display object identification information or other information about the object. In this embodiment, the signal may be sensed by the wrist-worn device, and the resulting data is also processed by/in the wrist-worn device. Alternatively, or additionally, the wrist-worn device may include sensors and storage and/or transmission circuitry and computing device 600 may be located elsewhere. In this embodiment, the signal is sensed by the wrist-worn device, and the resulting data is transmitted to computing device 600 for processing. Computing device 600 may be located locally to the wrist-worn device, or computing device 600 may be located remotely from the wrist-worn device, such as on a network or in the cloud.

Computing device 600 may include one or more processors (CPUs) 602A-602N, input/output circuitry 604, network adapter 606, and memory 608. CPUs 602A-602N execute program instructions in order to carry out the functions of the present invention. Typically, CPUs 602A-602N are one or more microprocessors, such as an INTEL ATOM® processor. FIG. 6 illustrates an embodiment in which computing device 600 is implemented as a single multi-processor computer system, in which multiple processors 602A-602N share system resources, such as memory 608, input/output circuitry 604, and network adapter 606. However, the present invention also contemplates embodiments in which computing device 600 is implemented as a plurality of networked computer systems, which may be single-processor computer systems, multi-processor computer systems, or a mix thereof.

Input/output circuitry 604 provides the capability to input data to, or output data from, computing device 600. For example, input/output circuitry may include input devices, such as keyboards, mice, touchpads, trackballs, scanners, analog to digital converters, sensors, etc., output devices, such as video adapters, monitors, printers, etc., and input/output devices, such as, modems, etc. Network adapter 606 interfaces device 600 with a network 610. Network 610 may be any public or proprietary LAN or WAN, including, but not limited to the Internet.

Memory 608 stores program instructions that are executed by, and data that are used and processed by, CPU 602 to perform the functions of computing device 600. Memory 608 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 608 may vary depending upon the function that computing device 600 is programmed to perform. In the example shown in FIG. 6, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present invention contemplates any and all such arrangements.

In the example shown in FIG. 6, memory 608 may include sensor data capture routines 612, signal processing routines 614, object identification routines, object identification data, and operating system 616. For example, sensor data capture routines cell data 612 may include routines that interact with one or more sensors, such as a microphone, accelerometer, gyroscope, etc., and capture data, such as noise or vibration signal data. Signal processing routines 614 may include routines to process the captured signal data and output corresponding digital data. Object identification routines 616 may include routines to use the processed digital data to access object identification data 618 to identify the object being interacted with. Object identification data 618 may, for example, be a database that provides the capability to lookup object identity information based on digital data. Operating system 620 provides overall system functionality.

As shown in FIG. 6, the present invention contemplates implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multitasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A computer program product for object identification, the computer program product comprising a non-transitory computer readable storage having program instructions embodied therewith, the program instructions executable by a computer, to cause the computer to perform a method comprising:
   receiving at least one of a vibration signal or an acoustic signal produced by a physical interaction with an object to be identified, the signal produced during physical interaction with the object by an identification structure coupled to the object;
   processing the signal to form digital data identifying the object interacted with; and
   accessing a database using the digital data to retrieve additional information identifying or describing properties of the object.

2. The computer program product of claim 1, wherein the identification structure comprises a plurality of bumps or teeth and the vibration signal comprises a vibration produced by pin or tooth rubbing against the bumps or teeth.

3. The computer program product of claim 1, wherein the identification structure comprises a plurality of bumps or teeth and the acoustic signal comprises a sound produced by pin or tooth rubbing against the bumps or teeth.

4. The computer program product of claim 1, wherein the plurality of bumps or teeth is arranged so as to encode identification information for the object.

5. The computer program product of claim 1, wherein the signal is produced during normal use of the object and the signal is captured by a device attached to a user.

6. The computer program product of claim 1, wherein the identification structure further comprises a portion corresponding to information identifying a manufacturer of the object.

7. An object comprising:
   at least one identification structure adapted to produce a sound upon physical interaction with the object, wherein the identification structure comprises a plurality of bumps or teeth and the physical interaction comprises a pin or tooth rubbing against the bumps or teeth.

8. The object of claim 7, wherein the plurality of bumps or teeth is arranged so as to encode identification information for the object.

9. The object of claim 7, wherein the identification structure further comprises a portion corresponding to information identifying a manufacturer of the object.

10. An object comprising:
at least one identification structure adapted to produce a vibration upon physical interaction with the object, wherein the identification structure comprises a plurality of bumps or teeth and the physical interaction comprises a pin or tooth rubbing against the bumps or teeth.

11. The object of claim 10, wherein the plurality of bumps or teeth are arranged so as to encode identification information for the object.

12. The object of claim 10, wherein the identification structure further comprises a portion corresponding to information identifying a manufacturer of the object.

* * * * *